(12) United States Patent
Wadle

(10) Patent No.: US 6,348,202 B1
(45) Date of Patent: Feb. 19, 2002

US006348202B1

(54) COSMETIC COMPOSITIONS CONTAINING DIHYDROXYACETONE AND METHODS OF STABILIZING THE SAME

(75) Inventor: Armin Wadle, Erkrath (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/319,297

(22) PCT Filed: Nov. 27, 1997

(86) PCT No.: PCT/EP97/06613

§ 371 Date: Jun. 4, 1999

§ 102(e) Date: Jun. 4, 1999

(87) PCT Pub. No.: WO98/24406

PCT Pub. Date: Jun. 11, 1998

(30) Foreign Application Priority Data

Dec. 5, 1996 (DE) .......................................... 196 50 473

(51) Int. Cl.⁷ ................................................. A61K 7/42
(52) U.S. Cl. ........................... 424/401; 424/59; 424/60; 424/78.03; 514/937
(58) Field of Search ........................... 424/401, 59, 60, 424/78.03; 514/937

(56) References Cited

U.S. PATENT DOCUMENTS

| 4,172,887 A | 10/1979 | Vanlerberghe et al. ......... 424/70 |
| 5,374,716 A | 12/1994 | Biermann et al. .......... 536/18.6 |
| 5,576,425 A | 11/1996 | Hill et al. ................... 536/18.6 |
| 5,620,681 A | 4/1997 | Takata et al. .................. 424/59 |
| 5,679,656 A | 10/1997 | Hansenne ..................... 514/54 |
| 5,840,943 A | 11/1998 | Ansmann et al. ........... 554/166 |

FOREIGN PATENT DOCUMENTS

| DE | 1 165 574 | 3/1964 |
| DE | 20 24 051 | 12/1971 |
| DE | 295 20 816 | 5/1996 |
| DE | 196 43 062 | 6/1997 |
| EP | 0 301 298 | 2/1989 |
| EP | 0 671 159 | 4/1995 |
| EP | 0 689 125 | 12/1995 |
| EP | 0 715 845 | 6/1996 |
| FR | 22 52 840 | 6/1975 |
| GB | 962 919 | 7/1964 |
| GB | 1 333 475 | 10/1973 |
| WO | 90/03977 | 4/1990 |
| WO | 95/34528 | 12/1995 |

OTHER PUBLICATIONS

J. Garces, et al., "Dihydroxyacetone in Microspheres: An Approach to Overcome DHA Drawbacks", Euro Cosmetics, No. 11, pp. 26–29 (1995).

*Kosmetische Farbemittel*, Third Edition, pp. 81–106, (VCH Verlagsgesellschaft mbH, Weinheim, 1991).

*Primary Examiner*—Raj Bawa
(74) *Attorney, Agent, or Firm*—John E. Drach; Thomas F. Roland; Aaron R. Ettelman

(57) ABSTRACT

A cosmetic preparation is presented containing (a) alkyl or alkenyl oligoglycosides (b) polyol poly-12-hydroxystearates and (c) dihydroxyacetone. This self-tanning cosmetic preparation has high dermatological compatibility, a favorable feeling on the skin and good storage stability at relatively high temperatures.

14 Claims, No Drawings

COSMETIC COMPOSITIONS CONTAINING DIHYDROXYACETONE AND METHODS OF STABILIZING THE SAME

This application is filed under 35 U.S.C. 371 and based on PCT/EP96/06613, filed Nov. 27, 1997.

BACKGROUND OF THE INVENTION

1. Field of the Invention

This invention relates to cosmetic preparations, preferably self-tanning preparations, containing selected nonionic emulsifiers and dihydroxyacetone and to the use of these emulsifiers for the production of the preparations.

2. Discussion of Related Art

In the modern meritocracy, many people associate a tanned skin with notions of "youth" and "dynamism". For consumers who are unable or do not wish to expose themselves either to natural or to artificial UV radiation, but still want a tanned skin, the cosmetic industry offers self-tanning preparations most of which contain dihydroxyacetone (DHA) as their active ingredient.

One problem of using DHA is that its stability in cosmetic products is often inadequate so that unwanted secondary reactions, for example the formation of formaldehyde or formic acid, can occur. This can generally be prevented by microencapsulation [Euro Cosm. No. 11, 26 (1995)]. Cosmetic o/w emulsions containing DHA which have a particle size of 100 to 1,000 nm are known from European patent application EP-A1 0 689 125 (L'Oreal). According to European patent application EP-A1 0 715 845 (L'Oreal), self-tanning preparations containing dihydroxyacetone are obtained by using a mixture of an alkyl polyglucoside and a fatty alcohol as emulsifier. In addition, compositions containing oils and ethylene oxide/propylene oxide block polymers in addition to DHA are known from European patent application EP-A1 0 671 159 (Shiseido).

Another problem is the fact that the preparations are generally homogeneous at room temperature and have a constant viscosity, but quickly develop an irreversible tendency to separate and lose their viscosity when heated, for example, to 35–40° C. If a preparation such as this is applied, the self-tanning ingredients are unevenly distributed over the skin with the result that the tanning effect appears patchy. It will readily be appreciated that this is not tolerable to the consumer.

Accordingly, the problem addressed by the present invention was to provide cosmetic preparations containing dihydroxyacetone which would be simultaneously distinguished by high dermatological compatibility, a favorable feeling on the skin and, in particular, by high stability in storage at relatively high temperatures. Accordingly, a key aspect of the problem addressed by the invention was to overcome the disadvantages of the prior art and reliably to prevent both the chemical decomposition of the DHA and the uneven distribution of the dihydroxyacetone when stored at elevated temperature in the preparations.

DESCRIPTION OF THE INVENTION

The present invention relates to cosmetic preparations containing
(a) alkyl and/or alkenyl oligoglycosides,
(b) polyol poly-12-hydroxystearates and
(c) dihydroxyacetone.

It has surprisingly been found that cosmetic preparations containing dihydroxyacetone which are distinguished by excellent stability in storage, even at elevated temperatures, can be obtained by using mixtures of alkyl and/or alkenyl oligoglycosides and polyol poly-12-hydroxystearates as nonionic emulsifiers. This ensures that the homogeneous, viscous compositions do not lose their stability, even in direct sunlight, and can be easily and reliably used by the consumer. At the same time, high stability of the DHA is observed without any need for microencapsulation.

Alkyl and/or alkenyl oligoglycosides

Alkyl and alkenyl oligoglycosides are known nonionic surfactants which correspond to formula (I):

$$R^1O\text{-}[G]_p \quad (I)$$

where $R^1$ is an alkyl and/or alkenyl radical containing 4 to 22 carbon atoms, G is a sugar unit containing 5 or 6 carbon atoms and p is a number of 1 to 10. They may be obtained by the relevant methods of preparative organic chemistry. EP-A1-0 301 298 and WO 90/03977 are cited as representative of the extensive literature available on this subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (I) indicates degree of oligomerization (DP), i.e. the distribution of mono-and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a non whole number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated C12 /$_{14}$ coconut oil fatty alcohol having a DP of 1 to 3 are preferred.

Polyol poly-12-hydroxystearates

The polyol poly-12-hydroxystearates are known substances which are marketed by Henkel KGaA of Dusseldorf, FRG, for example under the names of "Dehymuls® PGPH" and "Eumulgin® VL 75" (mixture with Coco Glucosides in a ratio by weight of 1:1). Reference is also made in this connection to International patent application WO 95/34528

(Henkel). The polyol component of the emulsifiers may be derived from substances which contain at least 2, preferably 3 to 12 and more preferably 3 to 8 hydroxyl groups and 2 to 12 carbon atoms. Typical examples are (a) glycerol and polyglycerol;

(b) alkylene glycols such as, for example, ethylene glycol, diethylene glycol, propylene glycol;

(c) methylol compounds such as, in particular, trimethylol ethane, trimethylol propane, trimethylol butane, pentaerythritol and dipenta-erythritol;

(d) alkyl oligoglucosides containing 1 to 22, preferably 1 to 8 and more preferably 1 to 4 carbon atoms in the alkyl group such as, for example, methyl and butyl glucoside;

(e) sugar alcohols containing 5 to 12 carbon atoms such as, for example, sorbitol or mannitol, (f) sugars containing 5 to 12 carbon atoms such as, for example, glucose or sucrose;

(g) amino sugars such as, for example, glucamine.

Among the emulsifiers suitable for use in accordance with the invention, reaction products based on polyglycerol are particularly important by virtue of their excellent applicational properties. It has proved to be of particular advantage to use selected polyglycerols which have the following homolog distribution (the preferred ranges are shown in brackets):

| | |
|---|---|
| glycerol | 5 to 35 (15 to 30) % by weight |
| diglycerols | 15 to 40 (20 to 32) % by weight |
| triglycerols | 10 to 35 (15 to 25) % by weight |
| tetraglycerols | 5 to 20 (8 to 15) % by weight |
| pentaglycerols | 2 to 10 (3 to 8) % by weight |
| oligoglycerols | to 100% by weight |

Components (a) and (b) may be mixed in a ratio of 90:10 to 10:90, preferably 75:25 to 25:75 and more preferably 60:40 to 40:60.

Oils

The preparations according to the invention preferably contain oils as further ingredients. Suitable oils are, for example, Guerbet alcohols based on fatty alcohols containing 6 to 18 and preferably 8 to 10 carbon atoms, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, more especially 2-ethyl hexanol, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more especially benzoic acid, vegetable oils, branched primary alcohols, substituted cycloyhexanes, linear $C_{6-22}$ fatty alcohol carbonates, Guerbet carbonates, esters of benzoic acid with linear and/or branched $C_{6-22}$ alcohols (for example Finsolv® TN), dialkyl ethers, silicone oils and/or aliphatic or naphthenic hydrocarbons.

In one preferred embodiment of the invention, the cosmetic preparations contain (a) 0.1 to 30, preferably 1 to 15% by weight alkyl and/or alkenyl oligoglycosides, (b) 0.1 to 30, preferably 1 to 15% by weight polyol poly-12-hydroxy-stearates, (c) 0.01 to 6, preferably 0.5 to 4% by weight dihydroxyacetone and (d) 1 to 90, preferably 25 to 75% by weight oils, with the proviso that the quantities shown add up to 100% by weight, optionally with water and typical auxiliaries and additives.

Commercial Applications

Preparations stable in storage, even at elevated temperatures, preferably self-tanning preparations in the form of o/w emulsions, are obtained with the nonionic emulsifier mixtures of alkyl and/or alkenyl oligoglycosides and polyol poly-12-hydroxystearates together with dihydroxyacetone. Accordingly, the present invention also relates to the use of mixtures of (a) alkyl and/or alkenyl oligoglycosides and (b) polyol poly-12-hydroxystearates as nonionic emulsifiers for dihydroxyacetone for the production of self-tanning preparations. One preferred embodiment of the invention is characterized by the use of mixtures containing (a) alkyl oligoglucosides and (b) polyglycerol poly-12-hydroxystearates in a ratio by weight of 25:75 to 75:25 and preferably in a ratio by weight of 40:60 to 60:40 and, in addition a polyol, preferably glycerol. Mixtures such as these are commercially available under the name of "Eumulgin® VL 75".

The preparations according to the invention, for example hair shampoos, hair lotions, foam baths, cremes, lotions or emollients, may additionally contain mild surfactants, co-emulsifiers, superfatting agents, stabilizers, waxes, consistency promoters, thickeners, cationic polymers, silicone compounds, biogenic agents, antidandruff agents, film formers, preservatives, hydrotropes, solubilizers, insect repellents, dyes and fragrances as further auxiliaries and additives.

Typical examples of suitable mild surfactants, i.e. surfactants with particular dermatological compatibility, are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, ether carboxylic acids, alkyl oligoglucosides, fatty acid gluc-amides, alkylamidobetaines and/or protein fatty acid condensates, preferably based on wheat proteins.

Suitable co-emulsifiers are, for example, nonionic surfactants from at least one of the following groups:

(1) products of the addition of 2 to 30 moles of ethylene oxide and/or 0 to 5 moles of propylene oxide to linear fatty alcohols containing 8 to 22 carbon atoms, to fatty acids containing 12 to 22 carbon atoms and to alkylphenols containing 8 to 15 carbon atoms in the alkyl group;

(2) $C_{12/18}$ fatty acid monoesters and diesters of products of the addition of 1 to 30 moles of ethylene oxide to glycerol;

(3) glycerol monoesters and diesters and sorbitan monoesters and diesters of saturated and unsaturated fatty acids containing 6 to 22 carbon atoms and ethylene oxide adducts thereof;

(4) adducts of 15 to 60 moles of ethylene oxide with castor oil and/or hydrogenated castor oil;

(5) polyol esters and, in particular, polyglycerol esters such as, for example, polyglycerol polyricinoleate;

(6) products of the addition of 2 to 15 moles of ethylene oxide to castor oil and/or hydrogenated castor oil;

(7) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);

(8) trialkyl phosphates and mono-, di- and/or tri-PEG-phosphates;

(9) wool wax alcohols;

(10) polysiloxane/polyalkyl polyether copolymers and corresponding derivatives;

(11) mixed esters of pentaerythritol, fatty acids, citric acid and fatty alcohol according to DE-PS 11 65 574 and/or mixed esters of fatty acids containing 6 to 22 carbon atoms, methyl glucose and polyols, preferably glycerol,

(12) polyalkylene glycols.

The addition products of ethylene oxide and/or propylene oxide with fatty alcohols, fatty acids, alkylphenols, glycerol monoesters and diesters and sorbitan monoesters and diesters of fatty acids or with castor oil are known, commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide with glycerol are known as refatting agents for cosmetic formulations from DE-PS 20 24 051.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known by the CTFA name of Cocamidopropyl Betaine is particularly preferred. Other suitable emulsifiers are ampholytic surfactants. Ampholytic surfactants are surface-active compounds which, in addition to a $C_{8/18}$ alkyl or acyl group, contain at least one free amino group and at least one -COOH or -SO$_3$H group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Other suitable emulsifiers are cationic surfactants, preferably esterquats and more particularly those of the methyl-quaternized fatty acid triethanolamine ester salt type.

The superfatting agents used may be such substances as, for example, lanolin and lecithin and polyethoxylated or acylated lanolin and lecithin derivatives, polyol fatty acid esters, monoglycerides and fatty acid alkanolamides, the latter also serving as foam stabilizers. Suitable consistency promoters are, above all, fatty alcohols containing 12 to 22 and preferably 16 to 18 carbon atoms and, in addition, partial glycerides. Suitable thickeners are, for example, polysaccharides, more particularly xanthan gum, guar guar, agar agar, alginates and tyloses, carboxymethyl cellulose and hydroxyethyl cellulose, relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols such as, for example, pentaerythritol or trimethylol propane, narrow-range fatty alcohol ethoxylates and electrolytes such as sodium chloride and ammonium chloride.

Suitable cationic polymers are, for example, cationic cellulose derivatives such as, for example, the quaternized hydroxyethyl cellulose available under the name of Polymer JR 400® from Amerchol, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat®L Grünau), quaternized wheat polypeptides, polyethyleneimine, cationic silicone polymers such as, for example, Amidomethicone, copolymers of adipic acid and dimethyl aminohydroxypropyl diethylenetriamine (Cartaretine®, Sandoz), copolymers of acrylic acid with dimethyl diallyl ammonium chloride (Merquat® 550, Chemviron), polyaminopolyamides as described, for example, in FR-A 225840 and crosslinked water-soluble polymers thereof, cationic chitin derivatives such as, for example, quaternized chitosan, optionally in microcrystalline distribution, condensation products of dihaloalkyls such as, for example, dibromobutane with bis-dialkylamines such as, for example, bis-dimethylamino-1,3-propane, cationic guar gum such as, for example, Jaguar® CBS, Jaguar® C-17, Jaguar® C-16 of Celanese, quaternized ammonium salt polymers such as, for example, Mirapol® A-15, Mirapol® AD-1, Mirapol® AZ-1 of Miranol.

Suitable silicone compounds are, for example, dimethyl polysiloxanes, methyl phenyl polysiloxanes, cyclic silicones and amino-, fatty acid-, alcohol-, polyether-, epoxy-, fluorine- and/or alkyl-modified silicone compounds which may be both liquid and resin-like at room temperature. Typical examples of fats are glycerides while suitable waxes are inter alia beeswax, carnauba wax, candelilla wax, montan wax, paraffin wax or microwaxes, optionally in combination with hydrophilic waxes, for example cetostearyl alcohol, or partial glycerides. The pearlescent waxes used may be, in particular, mono- and difatty acid esters of polyalkylene glycols, partial glycerides or esters of fatty alcohols with polybasic carboxylic acids or hydroxycarboxylic acids. Suitable stabilizers are metal salts of fatty acids such as, for example, magnesium, aluminium and/or zinc stearate. Biogenic agents in the context of the invention are, for example, tocopherol, tocopherol acetate, tocopherol palmitate, ascorbic acid, retinol, bisabolol, allantoin, phytantriol, panthenol, AHA acids, plant extracts and vitamin complexes. Suitable antidandruff agents are climbazol, octopirox and zinc pyrithione. Typical film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds.

In addition, hydrotropes such as, for example, ethanol, isopropyl alcohol or polyols may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols having an average molecular weight of 100 to 1,000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms such as, for example, sorbitol or mannitol;

sugars containing 5 to 12 carbon atoms such as, for example, glucose or sucrose and aminosugars such as, for example, glucamine.

Suitable preservatives are, for example, phenoxyethanol, formaldehyde solution, parabens, pentanediol or sorbic acid. Suitable insect repellents are N,N-diethyl-m-toluamide, pentane-1,2-diol or Insect Repellent 3535. Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106, These dyes are normally used in concentrations of 0.001 to 0.1% by weight, based on the mixture as a whole.

The total percentage content of auxiliaries and additives may be from 1 to 50% by weight and is preferably from 5 to 40% by weight, based on the particular formulation. The formulations may be prepared by standard cold or hot processes and are preferably produced by the phase inversion temperature method.

EXAMPLES

To prepare various o/w self-tanning lotions, the starting materials listed in Table 1 were mixed by the PIT method. Lotions 1 to 6 according to the invention and comparison lotions C1 and C2 were then stored for 2 days at 35° C. Viscosity was measured by the Brookfield method in an RVT viscosimeter (5 r.p.m., spindle 4) and was visually evaluated. The symbol (+) signifies a stable homogeneous emulsion while (−) signifies separation. The results are set out in Table 1.

TABLE 1

Stability of o/w self-tanning lotions in storage

| Component | 1 | 2 | 3 | 4 | 5 | 6 | C1 | C2 |
|---|---|---|---|---|---|---|---|---|
| Eumulgin ® VL 75[1] | 5.0 | 5.0 | 5.0 | 5.0 | 5.0 | 5.0 | — | — |
| Montanov ® 68[2] | — | — | — | — | — | — | 5.0 | 5.0 |
| Ceteareth-20 | — | — | — | — | 2.0 | — | — | 2.0 |
| Glyceryl stearate | 5.0 | 5.0 | 5.0 | 5.0 | 5.0 | 5.0 | 5.0 | 5.0 |
| Dihydroxyacetone | 2.0 | 2.0 | 2.0 | 2.0 | 2.0 | 2.0 | 2.0 | 2.0 |
| Titanium dioxide | — | 1.0 | — | 0.5 | — | 1.0 | — | — |
| Tocopherol acetate | — | — | 1.0 | 0.5 | — | 1.0 | — | — |
| Coco Glycerides | 10.0 | 10.0 | 10.0 | 10.0 | 10.0 | 10.0 | 10.0 | 10.0 |
| Oleyl oleate | 7.0 | 7.0 | 7.0 | 7.0 | 7.0 | 7.0 | 7.0 | 7.0 |
| Almond oil | 3.0 | 3.0 | 3.0 | 3.0 | 3.0 | 3.0 | 3.0 | 3.0 |
| Water | | | | to 100 | | | | |
| Stability in storage | | | | | | | | |
| - Viscosity (immediate, 20° C.) [mPas] | 7000 | 8000 | 7000 | 7000 | 5000 | 7000 | 7000 | 6000 |
| - Viscosity (after 2 d, 35° C.) [mPas] | 6900 | 7800 | 6900 | 7000 | 4800 | 6900 | 3500 | 4200 |
| - Stability (after 2 d, 35° C. | + | + | + | + | + | + | − | − |

Legend
1) Polyglyceryl-2 Dipolyhydroxystearate (and) Lauryl Glucoside (Henkel)
2) Cetearyl Glucoside (and) Cetearyl Alcohol (Seppic)

What is claimed is:

1. A cosmetic composition comprising:
   (a) an alkyl oligoglycoside, an alkenyl oligoglycoside or mixtures thereof;
   (b) a polyol poly-12-hydroxystearate; and
   (c) dihydroxyacetone.

2. The cosmetic composition of claim 1 wherein the alkyl or alkenyl oligoglycoside corresponds to the formula (I):

$$R^1O\text{—}[G]_p$$

wherein $R^1$ is an alkyl or alkenyl radical containing 4 to 22 carbon atoms, G is a sugar unit containing 5 or 6 carbon atoms and p is a number of 1 to 10.

3. The cosmetic composition of claim 1 wherein the alkyl or alkenyl oligoglycoside comprises an alkyl or alkenyl glucoside.

4. The cosmetic composition of claim 1 wherein the polyol poly-12-hydroxystearate comprises a polyglycerol poly-12-hydroxystearate.

5. The cosmetic composition of claim 1 wherein the weight ratio of the alkyl or alkenyl oligoglycoside (a) to the polyol poly-12-hydroxystearate (b) is from 90:10 to 10:90.

6. The cosmetic composition of claim 5 wherein the weight ratio of the alkyl or alkenyl oligoglycoside (a) to the polyol poly-12-hydroxystearate (b) is from 75:25 to 25:75.

7. The cosmetic composition of claim 6 wherein the weight ratio of the alkyl or alkenyl oligoglycoside (a) to the polyol poly-12-hydroxystearate (b) is from 60:40 to 40:60.

8. The cosmetic composition of claim 1 further comprising an oil.

9. The cosmetic composition of claim 8 comprising:
   (a) 0.1 to 30 percent by weight alkyl oligoglycoside, alkenyl oligoglycosides, or mixtures thereof;
   (b) 0.1 to 30 percent by weight polyol poly-12-hydroxystearates;
   (c) 0.01 to 6 percent by weight dihydroxyacetone; and
   (d) 1 to 90 percent by weight oil.

10. The cosmetic composition of claim 9 comprising:
    (a) 1 to 15 percent by weight alkyl oligoglycoside, alkenyl oligoglycosides, or mixtures thereof;
    (b) 1 to 15 percent by weight polyol poly-12-hydroxystearates;
    (c) 0.5 to 4 percent by weight dihydroxyacetone; and
    (d) 25 to 75 percent by weight oil.

11. The cosmetic composition of claim 1 further comprising 1 to 50 percent by weight of auxiliaries and additives.

12. The cosmetic composition of claim 11 further comprising 5 to 40 percent by weight of auxiliaries and additives.

13. An method for producing a self-tanning preparation comprising:
    (a) admixing an alkyl or alkenyl oligoglycoside with a polyol poly-12-hydroxystearate to form an emulsifier mixture; and
    (b) emulsifying dihydroxyacetate with said emulsifier mixture.

14. The cosmetic composition of claim 8 wherein the oil is selected from the group consisting of Guerbet alcohols based on $C_{16-18}$ fatty alcohols, esters of linear $C_{6-22}$ fatty acids with linear $C_{6-22}$ fatty alcohols, esters of branched $C_{6-13}$ carboxylic acids with linear $C_{6-22}$ fatty alcohols, esters of linear $C_{6-22}$ fatty acids with branched alcohols, esters of linear or branched fatty acids with polyhydric alcohols or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols with aromatic carboxylic acids, esters of Guerbet alcohols with aromatic carboxylic acids, vegetable oils, branched primary alcohols, substituted cyclohexanes, linear $C_{6-22}$ fatty alcohol carbonates, Guerbet carbonates, esters of benzoic acid with $C_{6-22}$ alcohols, dialkyl ethers, silicone oils, aliphatic hydrocarbons, naphthenic hydrocarbons, and mixtures thereof.

* * * * *